(12) United States Patent
Reiner (10) Patent No.: US 8,249,892 B2
(45) Date of Patent: Aug. 21, 2012

(54) METHOD OF DATA MINING IN MEDICAL APPLICATIONS

(76) Inventor: Bruce Reiner, Berlin, MD (US)

( * ) Notice: Subject to any disclaimer, the term of this patent is extended or adjusted under 35 U.S.C. 154(b) by 0 days.

(21) Appl. No.: 13/067,150

(22) Filed: May 12, 2011

(65) Prior Publication Data

US 2011/0218815 A1    Sep. 8, 2011

Related U.S. Application Data

(63) Continuation-in-part of application No. 12/137,926, filed on Jun. 12, 2008.

(60) Provisional application No. 61/344,042, filed on May 12, 2010, provisional application No. 60/929,081, filed on Jun. 12, 2007.

(51) Int. Cl.
G06Q 10/00 (2012.01)
G06Q 50/00 (2012.01)

(52) U.S. Cl. ........ 705/2; 705/3; 705/4; 700/90; 382/128

(58) Field of Classification Search ................ 705/2–4; 345/173, 179; 348/62, 92; 378/207; 382/115, 382/128, 131; 600/300; 702/81, 84
See application file for complete search history.

(56) References Cited

U.S. PATENT DOCUMENTS

| | | | |
|---|---|---|---|
| 7,349,859 | B1 | 3/2008 | Lamer et al. |
| 7,421,647 | B2 | 9/2008 | Reiner |
| 2003/0212580 | A1 | 11/2003 | Shen |
| 2006/0112069 | A1* | 5/2006 | Gentles et al. ........ 707/1 |
| 2007/0046649 | A1 | 3/2007 | Reiner |
| 2007/0106633 | A1 | 5/2007 | Reiner |
| 2007/0116336 | A1* | 5/2007 | Mahesh et al. ........ 382/128 |
| 2007/0118401 | A1 | 5/2007 | Mahesh et al. |
| 2007/0233520 | A1 | 10/2007 | Wehba et al. |
| 2007/0239376 | A1 | 10/2007 | Reiner |
| 2008/0154642 | A1* | 6/2008 | Marble et al. ........ 705/3 |

\* cited by examiner

*Primary Examiner* — Michelle Le
(74) *Attorney, Agent, or Firm* — Jean C. Edwards, Esq.; Edwards Neils PLLC (57) ABSTRACT

The present invention relates to a method of creating databases for data mining in medical applications. In one embodiment, the present invention relates to providing a data-driven objective reimbursement model incorporating performance and quality measures, tied to patient, exam, context, and provider-specific variables. In another embodiment, the present invention creates standardized databases where context, patient, provider, and technology specific variables are used to create an objective quantitative measure of exam complexity, which can be correlated with performance times and outcomes measures for iterative refinement. In another embodiment, through the combined analysis of examination complexity, interpretation accuracy, and interpretation times, specific to each individual radiologist, external pacers are created which can be customized to a radiologist's individual needs and preferences. The derived data is used to identify best practice patterns and end-user performance, which can be used by radiologists for individualized education and training.

23 Claims, 1 Drawing Sheet

METHOD OF DATA MINING IN MEDICAL APPLICATIONS

CROSS-REFERENCE TO RELATED APPLICATIONS

The present invention claims priority from U.S. Provisional Patent Application No. 61/344,042, filed May 12, 2010, and is a continuation-in-part of U.S. patent application Ser. No. 12/137,926, filed Jun. 12, 2008, the contents of both of which are herein incorporated by reference in their entirety.

BACKGROUND OF THE INVENTION

1. Field of the Invention

The present invention relates to creating databases where data mining for medical applications, can be performed.

2. Description of the Related Art

Current practices in medical applications are deficient in creating databases which can effectively be used by stakeholders in the healthcare industry.

While healthcare reform remains an important and timely topic for political and economic debate, all parties agree that balancing supply and demand within the delivery of healthcare services is critical to long term success. Unfortunately, the majority of healthcare consumers and service providers have very little understanding as to how physician reimbursements are calculated and modified, as medical practice trends and supporting technologies rapidly evolve.

Thus, while Pay for Performance (P4P) and Evidence-Based Medicine (EBM), which include data standardization and accessibility, and financial incentives tied to quality improvement, are standard, one could argue that the current reimbursement does not go far enough, and that a number of deficiencies exist related to transparency, accountability, accessibility, and quality. Accordingly, as the tenets of EBM and P4P become engrained within healthcare delivery, it is essential to modify the existing reimbursement model to reflect these principles. The opportunity to accomplish this goal is advanced through the continued evolution of information systems technologies and data mining. Thus, incorporating objective and standardized data into a transparent and accessible database, which can be used to enhance performance, education, and informed decision making, is needed.

In another problem associated with current practices, with the above stated continuing efforts to reduce medical reimbursements, many radiology service providers have reacted by increasing productivity, in order to maintain revenue. This continuing push to increase speed carries the risk of diminished quality, in the form of diagnostic accuracy. Thus, synergistically improving both productivity and quality, through the combined analysis of examination complexity, interpretation accuracy, and interpretation times, specific to each individual radiologist, is needed.

Finally, in another problem associated with current practices, EBM calls for the creation of "best practice" guidelines, leading to improved clinical outcomes, but one of the primary factors limiting EBM in radiology is the relative paucity of standardized databases. The creation of standardized medical imaging databases would offer the potential to enhance radiologist workflow and diagnostic accuracy through objective data-driven analytics; which can be categorized in accordance with specific variables relating to the individual exam, patient, provider, and technology being utilized.

Thus, the use of data mining in medical applications to solve all three issues, would greatly benefit diagnostic accuracy, workflow, and accountability.

SUMMARY OF THE INVENTION

The present invention relates to creating databases where data mining for medical applications can be performed.

In one embodiment, the present invention relates to providing an accountable and transparent reimbursement feature for incorporation of objective and standardized data into a transparent and accessible database, which can be used to enhance performance, education, and informed decision making. The present invention makes recommendations for creation of a data-driven objective reimbursement model incorporating performance and quality measures, tied to patient, exam, context, and provider-specific variables.

Specifically, the present invention is directed at: reducing the impact of politics and professional societal influence; creating an objective series of standardized metrics to use in reimbursement calculations; making all data readily accessible to interested parties, along with the methodology used to establish reimbursements; transitioning from a reimbursement model of effort to one of combined effort and effect; and incorporating data reflecting quality, clinical outcomes, and technology, tied to EBM and best practice guidelines.

Thus, with the heightened interest in P4P and EBM, the present invention creates standardized databases and a program which can record, track, and analyze a series of context, patient, provider, and technology specific variables. These data can in turn be used by the program to create an objective quantitative measure of exam complexity, which can be correlated with performance times and outcomes measures for iterative refinement. By making this data readily accessible, radiology service providers would gain education and training opportunities, while radiology consumers would be empowered to make well informed and educated decisions in service provider selection. In the end, healthcare reimbursements are tied to performance, through objective data mining and meta-analysis.

In another embodiment consistent with the present invention, data mining synergistically improves both productivity and quality, through the combined analysis of examination complexity, interpretation accuracy, and interpretation times, specific to each individual radiologist. The resulting technology can in turn be used by the program to create external pacers, which can be customized to the individual needs and preferences of each radiologist. The derived data can also be used by the program to identify best practice patterns and end-user performance, which can in turn be used by radiologists for individualized education and training.

Specifically, one medical data mining application of the present invention lies in productivity/workflow analysis and performance enhancement. Data-driven pacing offers the potential to improve radiologist productivity, workflow, and diagnostic accuracy. This can be accomplished by the program recording context and user-specific data within a longitudinal and iterative database, which can be analyzed to determine exam complexity and estimated task completion times. By developing functional components adaptable to the specific needs and preferences of each individual end-user, the program is customizable and adaptive to each individual practitioner. The ultimate goal of the present invention is to enhance productivity and workflow, improve diagnostic accuracy, provide customized education, and reduce cumulative fatigue through creative data mining and analysis.

In another embodiment consistent with the present invention, medical imaging data mining offers the potential to enhance radiologist workflow and diagnostic accuracy through objective data-driven analytics, which can be categorized in accordance with specific variables relating to the individual exam, patient, provider, and technology being utilized.

Regardless of the individual workflow strategy employed, the common denominator is data mining. Workflow derived data provides an objective tool for the program to evaluate cause and effect and also provides an objective method of assessing technology performance. In addition, data mining can provide valuable insight as to the relationship between workflow and quality, with the goal and objective of any workflow optimization strategy being the simultaneous improvement of productivity and quality.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to creating databases where data mining for medical applications can be performed.

Figure 1:
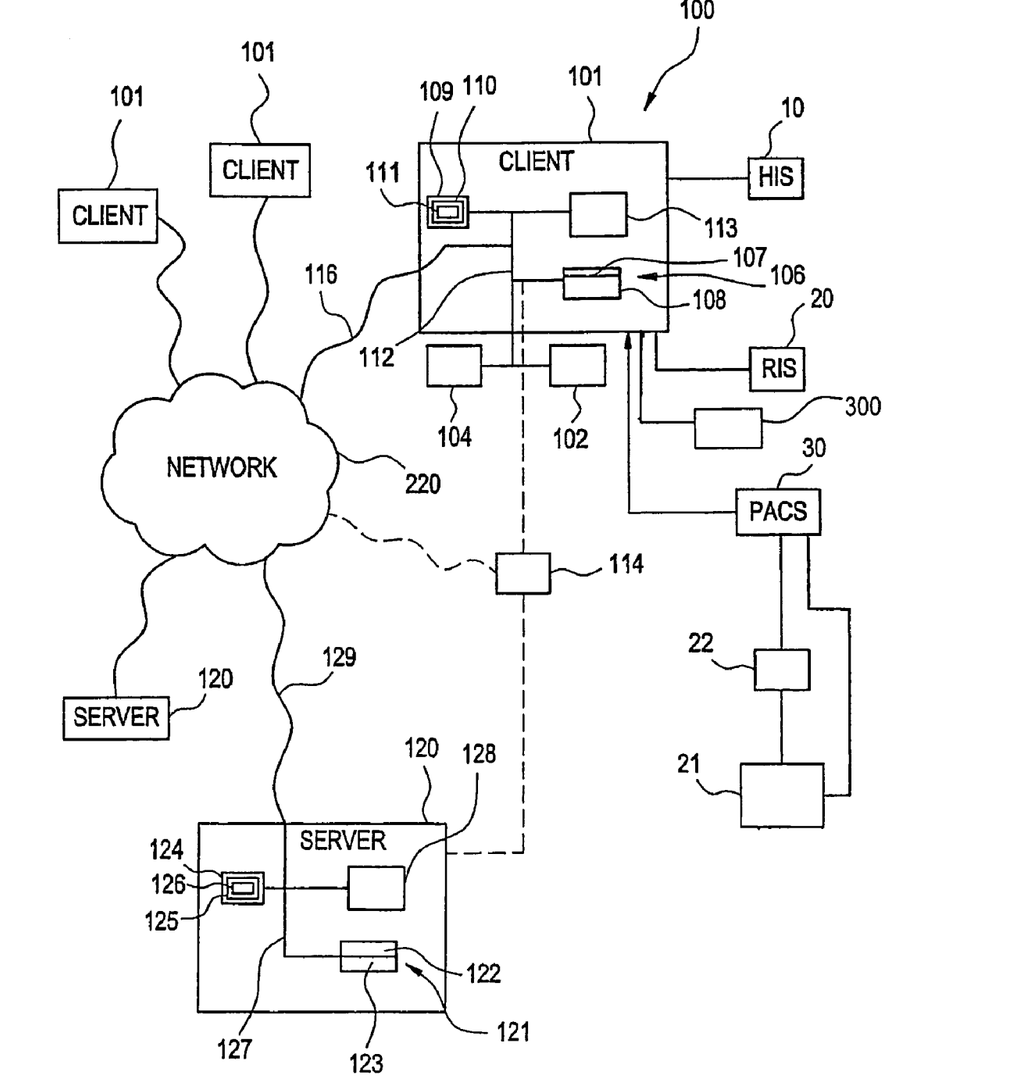
FIG. 1 is a schematic diagram showing the layout of the present invention.

According to one embodiment of the invention as illustrated in FIG. 1, medical (radiological) applications may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, radiographic device 21, CR/DR plate reader 22, and PACS 30, etc., may be enabled to allow the system 100 to retrieve and/or provide information from/to these systems. According to one embodiment of the invention, bi-directional communication between the system 100 of the present invention and the information systems, allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, eye-tracking system, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection. In another embodiment, an eye-tracking system is used to make commands and enter selections on the display 102.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS 30 and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system 100 of the present invention may be described as performing certain functions, one of ordinary skill in the art will readily understand that the program 110 may perform the function rather than the entity of the system 100 itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, or other forms of ROM or RAM either currently known or later developed. Further, although specific components of the system have been described, one skilled in the art will appreciate that the system suitable for use with the methods and systems of the present invention may contain additional or different components.

The present invention relates to creating databases where data mining for medical applications can be performed. In one embodiment consistent with the present invention, an accountable and transparent reimbursement feature provides for incorporation of objective and standardized data into a transparent and accessible database, which can be used to enhance performance, education, and informed decision making. The present invention overcomes the existing deficiencies in the current reimbursement model, and makes recommendations for creation of a data-driven objective reimbursement model incorporating performance and quality measures, tied to patient, exam, context, and provider-specific variables.

The current physician reimbursement model is based upon the Resource-Based Relative Value Scale (RBRVS), which is a quantitative measure of physician resource requirements to deliver a specific service. The derived relative value units (RVUs) are based upon three separate factors: physician work, practice expenses, and professional liability insurance. The physician work component accounts for 52% of the overall value and is a composite of physician time, mental effort, technical skill, judgment, and psychological stress.

However, the RBRVS deficiencies include: 1) lack of transparency and accountability; 2) payments based upon effort, not effect; 3) potential conflict of interest; 4) missing quality assessment; 5) static data analysis; 6) inaccessible data; and 7) no allowance for technology variability.

Further, several concerns have been raised regarding oversight, administration, and decision making. In addition, simultaneous control over reimbursement decision making and exclusive profitability raises concerns over a potential conflict of interest. Also, reimbursement under the RBRVS system being based upon effort, not effect, has the potential to lead to misaligned incentives on the part of service providers, who may prioritize profitability over quality.

Thus, rather than the current secretive process of establishing reimbursements, with few checks and balances, which creates concern over transparency and accountability, the present invention provides direct access to all data and decision-making, as well as creation of a system for outside input from all interested parties.

Accordingly, the present invention is directed at: reducing the impact of politics and professional societal influence; creating an objective series of standardized metrics to use in reimbursement calculations; making all data readily accessible to interested parties, along with the methodology used to establish reimbursements; transitioning from a reimbursement model of effort to one of combined effort and effect; and incorporating data reflecting quality, clinical outcomes, and technology, tied to EBM and best practice guidelines.

In an exemplary embodiment of the present invention, the various data elements which could be incorporated by the program 110 into such a model for radiology reimbursement are:

A. Patient Profile: Age, Gender, Genetics, Body habitus, Mobility, Compliance, Past Medical/Surgical history, Laboratory/Clinical test data, and Overall Clinical status.

B. Institutional Profile: Location, Patient population served, Academic status, Size, JCHAO scores, and Operational efficiency measures.

C. Imaging Profile:
 1. Prior imaging exams: Indication specific, and Modality specific.
 2. Prior imaging reports.

D. Technology Profile: Acquisition device, Information systems, Decision support tools.

E. Exam Profile: Clinical indication, Size and complexity of database, Image processing and reconstructions, Number of sequences, Contrast administration, and Overall quality of dataset.

These data elements include a series of profiles, which take into account unique attributes of the patient, institution, examination, and technology. The net result would be a composite measure of examination complexity, which can in turn be correlated by the program 110 with clinical outcomes of the service provider. Since clinical outcomes could not be determined prospectively, the provider outcomes profile run by the program 110 would be a retrospective analysis of past performance measures, which would be continuously updated by the program 110 as additional data is collected and analyzed by the program 110. This provides an incentive for each provider to review performance data and direct continuing education and training efforts at those areas which are lacking relative to their peer reference groups. The analysis of these quality measures by the program 110 would be categorized to reflect differences in the provider community, including education/training, experience, supporting technology, institutional profile, and geography.

To illustrate how the program 110 would be used to quantitatively determine examination complexity in accordance with the various profiles, the following example is of the commonly encountered head CT ordered by the emergency room physician for evaluation of altered mental status. By adjusting variables contained within the patient profile (e.g., age, past medical history), one can easily alter examination complexity.

For example, an 18 year old male with no significant past medical history would be expected to have a relatively straightforward diagnosis, as compared to a 75 year old male with a history of multiple strokes. At the same time, if the 75 year old male was non-compliant during the examination, resulting in motion artifact and repeated attempts at imaging, examination complexity would be further increased due to quality deficiencies along with the greater number of sequences for interpretation. If, for example, the 18 year old male was now found to have diagnosed AIDS, examination complexity would be increased, based upon the patient's clinical status and a large number of comparison brain imaging exams and reports requiring review.

In another example, a given patient was having the same imaging examination (e.g., chest CT) performed at two different institutions, using different technologies and protocols. At the first institution, the examination is performed on a 4 detector CT scanner and imaged in the axial plane only, without reconstructions. The second institution acquires the examination on a 64 detector CT and performs multi-planar reconstructions, with segmentation. While both exams are performed on the same patient for the same clinical indication, the corresponding complexity and expected interpretation times would be quite different.

Unfortunately, the current reimbursement model does not adequately address variations in patient, institutional, technology, imaging, and exam profiles. A radiologist would be paid essentially the same fee for interpreting the "healthy" 18 year old head CT with no comparison imaging data, and the "sickly" 75 year old head CT with extensive comparison imaging data. This economic disparity can often result in the practice of "cherry picking", where individual physicians select out exams from the unread queue, in accordance with the perceived ease of diagnosis.

However, with the present invention, by creating an objective database 113, 114 where the program 110 can quantitatively measure exam complexity, compensation can be more fairly distributed, preventing such practices.

In addition, as more data is recorded into the database 113, 114 by the program 110, and feedback is provided to the user by the program 110 based upon outcomes (e.g., diagnostic accuracy) and efficiency measures (e.g., interpretation time), the database 113, 114 becomes more refined in an iterative fashion.

A number of other administrative applications can be derived by the program 110 from the database 113, 114, such as improved workflow distribution, operational efficiency, and staffing. A radiology department chief or administrator could utilize the database 113, 114 to determine optimal routing of exams in accordance with exam complexity and the quality profiles of available radiologists. The value of such a system would be enhanced in a multi-institutional group or teleradiology practice. At some point in time, teleradiology providers may elect to migrate from the current fixed pricing model to a more flexible model, tied to exam complexity measures and quality deliverables. This has the added benefit of counteracting existing commoditization trends within the radiology service community.

In addition to economic reimbursement, the database 113, 114 can also be used by the program 110 to analyze medico-legal risk and provide a fair, reproducible, and objective method for defining malpractice rates on an individual basis. A radiologist practicing in a small rural hospital with a case mix of low complex exams on relatively healthy patients would have objective data to request lower medical malpractice rates than a radiologist practicing in a similar sized hospital, performing a more complex case mix on sicker patients (assuming their quality performance measures are comparable). Consumers of the medical services (e.g., patients, third party payers) can utilize the data to make well informed and data-driven decisions as to the selection of service providers.

As an example, an institution seeking to outsource a portion of their professional radiology services to a teleradiology provider can correlate their own institutional and exam profiles, with the performance measures of prospective teleradiology providers to identify the best fit for their needs; based upon cost, operational efficiency, and outcomes.

Thus, with the heightened interest in P4P and EBM, the present invention creates standardized databases 113, 114, and a program 110 which can record, track, and analyze a series of context, patient, provider, and technology specific variables. These data can in turn be used by the program 110 to create an objective quantitative measure of exam complexity, which can be correlated with performance times and outcomes measures for iterative refinement. By making this data readily accessible, radiology service providers would gain education and training opportunities, while radiology consumers would be empowered to make well informed and educated decisions in service provider selection. In the end, healthcare reimbursements are tied to performance, through objective data mining and meta-analysis.

In another embodiment consistent with the present invention, data mining synergistically improves both productivity and quality, through the combined analysis of examination complexity, interpretation accuracy, and interpretation times, specific to each individual radiologist. The resulting technology can in turn be used by the program 110 to create external pacers, which can be customized to the individual needs and preferences of each radiologist. The derived data can also be used by the program 110 to identify best practice patterns and end-user performance, which can in turn be used by radiologists for individualized education and training.

The medical data mining of the present invention is used in a number of applications within medical imaging, including the creation of best practice guidelines (i.e., evidence-based medicine), improving patient safety (e.g., radiation and contrast optimization), and assessment of quality deliverables among various stakeholder groups. These data mining applications share the common goal of enhancing clinical outcomes, which is the most important goal in medicine.

Another medical data mining application of the present invention lies in productivity/workflow analysis and performance enhancement. In its current form, individual and departmental productivity is measured using fairly crude data such as examinations per full-time equivalent (FTE) and relative value units (RVUs). These data are largely the vestige of the analog radiology practice, where complexity in technology, imaging datasets, and workflow were less pronounced than in current practice.

To perform accurate productivity analysis, the use of external pacers to enhance speed and athletic performance is well known. The common theme in these athletic pursuits is the search for improved performance, through enhanced productivity and workflow, mainly using computers and statistical analysis. However, few technological adaptations have migrated into the medical (imaging) domain.

Due to the current economic challenges and continuing trend towards reimbursement reductions, imaging departments are trying to maintain revenue through increased productivity. At the same time however, medical imaging professionals must be cognizant of the fact that increasing productivity has the potential to adversely affect quality, in the form of diagnostic accuracy. In order to solve these problems, the present invention utilizes a technology which could simultaneously enhance productivity and quality.

Before integrating external pacing technologies into radiologist workflow, a standardized database 113, 114 is created by the program 110 in order to objectively quantify exam complexity, which is the principle determinant in predicting interpretation time requirements. The methodology for creating such a database 113, 114 includes having the program 110 record in the database 113, 114 a number of variables which would reflect variations specific to the individual patient, examination, technology, clinical context, and historical imaging record. Each variable could be assigned a numerical value on a sliding scale by the program 110, the value which would be weighted in accordance with its perceived relative importance. The sum total of these data would have a comprehensive complexity score generated by the program 110, which could in turn be used by the program 110 to estimate task completion time.

The computerized sources for these data would include the imaging modality, radiology information system (RIS), electronic medical record (EMR), computerized physician order entry system (CPOE), and picture archival and communication system (PACS). If not available through computer database 113, 114 by retrieval by the program 110, human data sources could be used, including the ordering clinician, technologist, radiologist, and patient.

Once a given exam's complexity score is determined by the program 110, an estimated exam interpretation time can be derived by the program 110 which can take into account the individual radiologist profile, including: Age, Training, Experience, Exam Proclivity, Historical Speed, Historical Accuracy, and Technology Utilized. This radiologist-specific profile takes into account variables related to individual experience/training, historical record of interpretation speed/accuracy, and exam-specific attributes. The purpose of this profile is to provide a means with which each individual radiologist's strengths and weaknesses can be prospectively factored into the analysis by the program 110, in order to provide a realistic and reproducible estimate of task completion. Due to the fact that this profile score is dynamic in nature, it can be adjusted over time by the program 110 in accordance with changes in radiologist practice patterns, proclivity towards different exam types, and utilization of different technologies.

As an example, a radiologist's proficiency for a given exam type/pathology may improve over time commensurate with educational pursuits, changes in technology utilized, and/or clinical experience. As these factors come into play, each individual radiologist's profile will become automatically upgraded by the program 110 to reflect expected productivity changes.

The derived interpretation time estimates can in turn be correlated by the program 110 with actual time estimates, to create a dynamic database 113, 114, which is updated by the program 110 to reflect differences between estimated and actual measures.

Historical productivity data can also be integrated by the program 110 into the derived time estimates. As an example, if a same radiologist is interpreting a follow-up study on the same patient, both the derived time estimate and historical actual measurements would be presented by the program 110. The end result is the creation of an iterative database 113, 114 which takes into account user and context-specific variables, along with historical performance data.

Once the data has been calculated by the program 110 and presented for review, the radiologist is provided with a number of data and functional options for use. These options include:

A. Data Options:
1. Estimated interpretation time (radiologist-specific)
2. Estimated interpretation (peer reference group)
3. Estimated interpretation time (all radiologists)
4. Historical interpretation time (same patient and exam type)
5. Calculated exam complexity B. Functional Options
1. Pacer on or off
2. Method of prompts
3. Method of analysis
4. Individual and/or cumulative exam analysis
5. Method of feedback In one application, the radiologist may utilize this data to assist in exam selection from the unread study queue. As an example, a radiologist may elect to choose higher complexity cases early in the working day and shift to lower complexity cases as the day progresses and stress/fatigue increases. Alternatively, a sub-specialist radiologist may elect to focus on specific exam types, in accordance with his/her specialty expertise. The quantitative method of analysis by the program 110 provides a mechanism to accurately reflect exam complexity, thereby providing a potential incentive/reward system for radiologists interpreting exams of greater complexity. Radiologists would quickly learn to adapt to their own inherent strengths and weaknesses and have a guide to facilitate ongoing educational efforts, technology utilization, and workflow optimization.

To illustrate how the various data and functional options can be integrated into workflow by the program 110, one example is a general radiologist working within a community hospital practice. Based upon the pre-defined radiologist's preferences, the selected pacer options presented by the program 110 are as follows:

1. Estimated interpretation time
2. Calculated exam complexity
3. Pacer: on
4. Prompting mode: Auditory
5. Feedback interval: 50%, 100%
6. Individual exam analysis: Yes
7. Cumulative exam analysis: Yes
8. Cumulative analysis display: Racing graphics As each case is opened on the display by the program 110, the radiologist is provided by the program 110 with his/her personal estimated interpretation time along with the numerical exam complexity measure. In the early part of the day, the radiologist does not apply any filter to which exams are presented on his queue. As each case proceeds, he/she is provided with auditory cues, with specific sounds emitted when 50% and 100% of the estimated time measures have elapsed. Early on in the day, the radiologist is beating the estimated time measures, but eventually begins to slow as fatigue sets in. When he/she reviews the cumulative analysis graphics (which has been selected to be displayed in a race car format), he/she would see that they are 10% ahead of estimates in hour one, 6% ahead of estimates in hour 2, and 1% below estimates in hour 3. In determining the best course of action, to respond to this slowly deteriorating productivity (relative to time estimates), the radiologist can select from a few options:

1. Take a short break.
2. Adjust case selection by applying filters to the queue.
3. Request for automated workflow assistance.
4. Turn pacer off.

The radiologist elects to adjust case selection by applying a filter to the exam queue. The filter options include exam type, modality, clinical indication, historical imaging record, and exam complexity. The radiologist selects the modality and exam complexity options, and inputs into the computer the specific modalities of interest along with the range of desired exam complexity. In this example, the radiologist selects radiography as the desired modality, and exam complexity <50.

As the radiologist proceeds with interpretation, the program 110 presents updated graphic displays which report interval increases in productivity, which now measure 4% above the calculated estimates. As stress begins to increase, the measured productivity begins to decrease, so that in the second hour of post-filtering, the recorded productivity has decreased to 1% above estimates. At this point in time, the radiologist elects to turn the pacer off and continue reading. While auditory prompts and graphical analysis are no longer actively presented by the program 110, data continues to be collected by the program 110 in the background and available for review.

With respect to the how the electronic performance monitoring (EPM) tool of the present invention will be used by third parties, such as hospital administrators, department chiefs, or third party payers, in the case of radiologists, EPM provides the potential for physician empowerment in economic, educational, and technological terms. From an economic standpoint, the radiologist who utilizes the data to its fullest extent can potentially improve productivity, which in a fee for service practice environment translates into greater revenue. From the educational perspective, the derived data by the program 110 can provide insights to each individual radiologist, identifying specific opportunities for improvement, in terms of both productivity and diagnostic accuracy. From the technical perspective, data can be utilized by the program 110 to identify how specific technologies can be most efficiently utilized to enhance performance. By the program's 110 incorporating electronic auditing tools into the analysis, an individual radiologist can compare his/her own workflow with that of more efficient peers, in order to improve individual performance and technology utilization.

In order to address concerns over privacy and illicit use, the program 110 allows the radiologists to have direct input in determining how the data will be used and accessed. Research has shown that EBM related productivity gains and worker satisfaction are increased when individual workers are directly involved in the setting of productivity goals and establishing work standards, educational and training opportunities are incorporated, and well defined economic incentives are provided for performance improvement.

In order to guarantee long-term success and the desired productivity gains, the present invention provides radiologists with a degree of flexibility and autonomy as to how the technology will be implemented. Thus, the goals of the present invention are to create a pacing tool which will be proactive, customizable, and objective. Proactivity involves data delivery at the point of care, translating into tangible performance improvement. Customizing involves the incorporation of radiologist-specific preferences, allowing the technology to adapt to the specific needs and preferences of each individual end-user. Objectivity refers to the creation of standardized databases, which can be analyzed and used to define best practice guidelines and recommendations.

Thus, the present invention provides a data-driven analytical tool aimed at improving radiologist productivity and workflow, and incorporates correlative measures of diagnostic accuracy. A methodology of the present invention for creating a data-driven analysis of quality deliverables within medical imaging could be integrated by the program 110 into the overall performance data analysis. A number of methods exist to quantify diagnostic accuracy including radiologist peer review, surgical/pathology correlation, clinician feedback, correlation with serial imaging data, and correlation with clinical data contained within the EMR (e.g., discharge summaries). Due to the fact that the assessment of report diagnostic accuracy is largely a retrospective endeavor, corresponding productivity/quality analysis by the program 110 would also be retrospective. As a result, the incorporation of quality data into the proposed technology would be based upon individual radiologist and exam specific historical data. The combined productivity/quality data could provide insight to each radiologist, with the program 110 alerting them as to potential areas of concern. If the program 110 with the combined radiologist and exam profile database 113, 114, were to alert the radiologist as to a potential quality deficiency, options aimed at improving performance (in both productivity and quality measures), would be presented, including the following:

1. Select another exam (with more favorable exam profiles)
2. Identify the specific quality deficiencies from exams with similar profiles.
3. Adjust the estimate productivity measures (i.e., estimated interpretation time), to accommodate for historical quality deficiencies.
4. Provide automated workflow templates with associated high quality measures, for similar exam and radiologist profiles.

If the option to modify exam selection was chosen, the reading queue would be updated by the program 110 to reflect those unread exams which have been shown to have historically high diagnostic accuracy scores. Using this tool, the radiologist would be encouraged to interpret those exams best suited to his/her individual profile, based upon historical performance. While the practicality of exercising such an option may be limited in small practice settings, larger multi-institutional and teleradiology practice environments would be well suited to utilize this option.

The identification of quality deficiencies commensurate with the exam profile by the program 110, is a valuable quality assurance (QA) tool, which can be used to assist radiologists with targeted education and training programs. In addition to identifying specific areas of concern, the program 110 can be used to provide representative examples for individualized training.

As an example, a radiologist who has been shown to have difficulty interpreting subtle pulmonary emboli within second and third order pulmonary arteries, could have the program 110 present him/her with studies and reports fulfilling these search criteria. The radiologist could in turn retrieve these cases for review, and have the program 110 automatically replay the workflow used for original interpretation.

Adjustment of the estimated time measures by the program 110 is another method of support, based upon the established productivity and quality performance measures of the individual radiologist, in correlation with the specific exam profile. In the previously cited example of the chest CT angiography, it is determined by the program 110 that a given radiologist's diagnostic accuracy has been found to decrease when certain productivity measures are exceeded (i.e., shorter reading times produce lower quality scores). The program 110 can make a data-driven recommendation as to the optimal interpretation time (taking into account the exam and radiologist profiles), and use the pacer technology to help the radiologist "slow down". This illustrates an important component of the present invention, in that the proposed pacer technology is not always intended to "speed up" radiologist workflow, but can also be used to "slow down" workflow, in order to optimize diagnostic accuracy. The ultimate goal is for the program 110 to provide radiologists with intelligent and customized feedback in order to optimize productivity, diagnostic accuracy, and technology utilization.

Thus, data-driven pacing offers the potential to improve radiologist productivity, workflow, and diagnostic accuracy. This can be accomplished by the program 110 recording context and user-specific data within a longitudinal and iterative database 113, 114, which can be analyzed to determine exam complexity and estimated task completion times. By developing functional components adaptable to the specific needs and preferences of each individual end-user, the program 110 is customizable and adaptive to each individual practitioner. The ultimate goal of the present invention is to enhance productivity and workflow, improve diagnostic accuracy, provide customized education, and reduce cumulative fatigue through creative data mining and analysis.

In another embodiment consistent with the present invention, medical imaging data mining offers the potential to enhance radiologist workflow and diagnostic accuracy through objective data-driven analytics, which can be categorized in accordance with specific variables relating to the individual exam, patient, provider, and technology being utilized.

With the relative paucity of standardized databases in current radiological practice, the present invention enhances radiologist workflow and diagnostic accuracy through objective data-driven analytics. In addition to this "global" database analysis, "individual" radiologist workflow can be analyzed by the program 110 through the integration of electronic auditing tools into the PACS. The combination of these "individual" and "global" analyses can ultimately have the program 110 identify best practice patterns, which can be adapted to the individual attributes of the end-user, and ultimately be used in the creation of automated EBM workflow templates.

Data mining presents the medical imaging community with a number of opportunities relating to improved research, education, decision support, technology development, and creation of best practice guidelines. The program 110 interrelated with the standardized medical imaging databases 113, 114 of the present invention, can record, track, and analyze a series of context, patient, provider, and technology specific variables. Using these objective data, valuable insight can be gained by identifying the factors affecting radiologist effort and effect, which to date has been largely cursory and anecdotal in nature, in the absence of rigorous data analysis. The creation of standardized databases 113, 114 provides an opportunity for longitudinal, meta-analysis by pooling multi-institutional data, thereby providing large scale statistical analysis by the program 110, with the ability of the program 110 to explore the interaction effect of confounding variables.

In addition, the program 110 of the present invention will include electronic auditing tools which can incrementally record and track human-computer interactions, in order to gain an in-depth and detailed understanding of how workflow is influenced by context, technology, and user-specific variables. This type of computerized performance analysis is already being used in sports, where modern athletes are evaluated by sports scientists using advance computer technologies and statistical analysis to analyze motion; in the forms of imperceptible weight shifts, angle adjustments, and body motions. In the case of the radiologist, the goal is to streamline workflow through an economy of movement and optimal technology utilization, while maximizing performance outcomes in the forms of interpretation time and diagnostic accuracy.

With the lack of rigorous and customized technology education, which diminishes workflow, productivity, and clinical outcomes, the present invention provides a unique opportunity for informatics research, educational software development, and technology innovation. Although radiology practice is heterogeneous in nature, there is marked inter-radiologist variability, and since workflow is highly technology-dependent, workflow optimization by radiologists requires technology adaptability. With radiology workflow being context-specific which varies in accordance with technical, clinical, and historical imaging data, the present invention incorporates education and training in an effective workflow optimization strategy which includes quality improvements, and which can be customized to the specific needs and attributes of the individual radiologist. The present invention provides for longitudinal data mining, and automation, in the creation of "best clinical practice" guidelines, and can be used to provide customized end-user feedback for continuous improvement.

The present invention addresses inter-radiologist variability, which is multi-factorial in nature, and the result of a number of variables including age, education/training, experience, computer proclivity, personality, stress and fatigue. An example of intra-radiologist workflow variability can be seen as the day progresses, when most radiologists begin to experience progressive levels of stress and/or fatigue. Most radiologists adapt by increasing the frequency or duration of breaks, while others may continue to work on. In addition to slowing down with progressive levels of fatigue, radiologists may opt to adjust workflow by decreasing use of workstation tools, reducing comparison with historical imaging data/reports, or increasing their reliance on decision support technologies. Regardless of the strategy employed, it is important to realize that workflow constantly changes, and workflow modifications alter productivity and quality, and compensatory strategies should be developed for optimization.

Data-driven analysis by the program 110 in correlating changes in technology and workflow can provide insight as to how workflow can be modified in accordance with each individual technology to optimize radiologist performance. In addition to technology, workflow changes also occur in accordance with the context and individual user, and the program 110 is able to adapt to the task requirements and preferences/attributes of each individual end-user.

Workflow optimization is an iterative process which requires constant feedback, analysis, and refinement by the program 110. Feedback is provided to the end-user through the program's 110 electronic educational/training tools, to track each radiologist and the relationship between their computer actions, and their productivity, and outcomes. In the absence of computer-based educational/training software, radiologists will likely under-utilize available technology or use it in an inefficient fashion. The creation of automated workflow templates by the program 110 provides an opportunity for education, improved workflow, and technology optimization. When integrated directly into PACS 30, these automated workflow templates could be selected at the time and choosing of each individual radiologist.

Regardless of the individual workflow strategy employed, the common denominator is data mining. Workflow derived data provides an objective tool for the program 110 to evaluate cause and effect and also provides an objective method of assessing technology performance. In addition, data mining can provide valuable insight as to the relationship between workflow and quality, with the goal and objective of any workflow optimization strategy being the simultaneous improvement of productivity and quality.

In implementation of workflow optimization, the electronic auditing tool of the program 110 records all of the individual human-computer interactions an end-user (e.g., radiologist) goes through in the performance of a task, such as interpretation of an imaging exam. This data would in turn be automatically recorded by the program 110 into an electronic database 113, 114 using an XML schema, which allows for a number of downstream applications including detailed workflow analysis, automated playback, and correlation with clinical, technical, and performance data for productivity/workflow and outcomes analyses.

In addition to the "manual" interactions (i.e., manual workflow) recorded in the database 113, 114 by the program 110, the program 110 records, tracks, and analyzes "visual" interactions (i.e., visual workflow). Visual workflow analysis can be performed by tracking eye movements using commercially available eye tracking systems (i.e., by Applied Sciences Laboratory System), which samples eye movements every $\frac{1}{60}^{th}$ of a second to generate x and y coordinate eye-positioning data. A number of visual data can be recorded and incorporated into the visual workflow analysis by the program 110, including: glaze rate, gaze direction, gaze percentage, number of fixation (voluntary and involuntary), fixation duration, fixation rate, scan path directionality (length and duration), number of fixations over area of interest (AOI), number of instances of backtracking, frequency of long duration dwells over AOI, saccade length, and fixation/saccade time ratio.

In the normal course of image review and interpretation, a radiologist will often follow a pre-defined set of visual, cognitive, and manual steps. These predictable workflow patterns are based upon a number of exam, technology, and user-specific variables, including anatomy, modality, clinical data, historical imaging data, technology utilized, and individual end-user experience and training. Once these "visual" and "manual" workflow patterns have been established in accordance with these context and user-specific variables, automated workflow templates can be created by the program 110. The analysis and playback of these "manual" and "visual" workflow patterns can be used by the program 110 to create optimized exam and user-specific automated workflow protocols, by correlating them with performance measures (e.g., interpretation time, diagnostic accuracy). Those workflow templates which have been demonstrated to exhibit the highest data-derived performance measures can be used by the program 110 in the creation of "best practice" automated workflow templates; which can be categorized by the program 110 in accordance with the technical, clinical, and end-user profiles.

In one example, a chest CT angiogram is performed to assess pulmonary embolism, using an MPR workstation for interpretation. In the course of visual workflow analysis, three separate eye tracking patterns are identified by the program 110:

1. Geographic sweep: Eye tracking begins in the upper left hand corner of the image and proceeds across and down in a sequential fashion.

2. Bisection: Image is divided into left and right laterality, with eye tracking performed on each side individually.

3. Segmentation: Anatomy is divided according to organ system (e.g., arteries, lung fields, ribs), with each organ system individually and sequentially viewed, followed by a single comprehensive sweep of the combined dataset.

When analyzing the manual workflow, a number of distinct variables are identified by the program 110 including the following:

1. Integration of decision support software (e.g. CAD).
2. Image display in various 2-dimensional planes (e.g. axial, sagittal, coronal)
3. Reconstructions of dataset using 3-D and MIP
4. Manual versus pre-defined window/level adjustment When correlating the different workflow patterns and performance measures of multiple radiologists, the program 110 determines that "optimal" workflow differs in accordance with radiologist profile. Sub-specialist thoracic radiologists with the highest performance data tend to use the segmentation eye tracking pattern, without decision support, and with combined 2 and 3-D reconstructions. General radiologists are divided by the program 110 into two distinct groups, based upon computer proclivity. Those with high computer proclivity use the bisection eye tracking pattern, integration of CAD, pre-defined window/level adjustment, and multi-planar image review.

Those general radiologists with lower computer proclivity have optimized performance measures using the bisection eye tracking pattern, with CAD, image display in the axial plane only, and without reconstructions. As a result of this analysis by the program 110, when a radiologist requests from the program 110, an automated workflow template for chest CT angiography using an MPR workstation, he/she will be presented by the program 110 with the optimized viewing and manual workflow template that corresponds with his/her individual profile.

The present invention foresees that "visual" and "manual" workflow analyses may eventually become one, as visual input supplants manual input. Visual input has already proven to be useful in aviation and patients with loss of voluntary motor control. Research has shown that visual input commands can be twice as fast as conventional manual input. In addition, visual input through eye tracking also offers the unique advantages of eliminating the "wasted" visual effort associated with manual input devices.

The present invention encompasses the creation of "best practice" automated workflow templates, which can be customized by the program 110 to the individual end user, technology employed, and clinical context. While the primary goals of this invention are improved workflow and outcomes, a number of other applications can be derived, including improved: Objective measures of exam complexity, Workflow distribution, Customizable Pacing tool, Administrative assessment, Quality assurance, Economics, Education and training, Evidence-based medicine, and Technology assessment.

These derived benefits are not exclusive to radiology and can be applied to a number of medical disciplines and stakeholders. As an example, the quantitative means for determining the complexity of a given task and estimated time measures can also be applied to technologists (e.g., image acquisition), clinicians (e.g., consultation), or surgeon (e.g., operative procedure). In the example of an interventional procedure, the interventional radiologist or surgeon could input the patient name, procedure to be Performed, and institution of choice into the database 113. The program 110 would retrieve the corresponding clinical, technical, institutional, and provider data to calculate the procedural complexity and estimated task completion time. If any specific outliers are identified by the program 110 within the database 113, 114 (e.g., prior complications), these could be highlighted to assist in surgical planning and potential interventions. The patient could perform the same exercise, and receive comparative data for different institutional or individual service providers.

Quality assurance (QA) is an especially valued derivative of the present invention. The program 110 can not only provide a quantitative measure of exam complexity, but also identify historical and potential outliers related to outcomes. For example, a radiologist or QA administrator wanted to retrospectively evaluate cases with associated poor performance measures; which could take the form of prolonged interpretation times, misdiagnoses, or even qualified reports. Retrospective analysis of workflow used during the performance of the task could be performed by the program 110, along with salient review of associated data, to determine contributing factors.

As an example, the radiologist may want to review his/her report database 113, 114 to determine which exams had associated interpretation times which exceeded 125% of the time estimates or been associated with misdiagnosis. In retrieving this list of exams, the radiologist then queried the program 110 to identify any common denominators. By reviewing the retrieved list of common data elements, the radiologist may gain insight as to specific variables (e.g., clinical indication, acquisition parameters) which have had a negative effect on his/her performance. The radiologist may then go one step further by reviewing the computerized workflow analysis generated by the program 110 and associated with a few of these cases, and comparing his/her individual workflow analyses with those of more efficient users. In the course of this analysis, the radiologist may gain insight as to how certain technologies, applications, or workstation tools may be under or over-utilized.

Due to the dynamic nature of the program 110 and the ability to analytically review exam-specific workflow, retrospective QA analysis becomes more robust and provides for customized feedback, along with well defined areas for educational and training opportunities. In addition to manual queries, the program 110 can be configured to create automated alerts based upon pre-defined QA criteria.

Once the workflow data is correlated by the program 110 with performance data, the opportunities for education, training, and establishment of EBM guidelines is expanded. The creation of standardized data by the program 110 provides a mechanism to combine multi-institutional data and perform meta-analysis; which is a core requirement for EBM. In addition to providing educational insight to practitioners, the program 110 can also prove to be valuable to healthcare and technology consumers, who can utilize the data for educated and well informed decision-making.

As an example, a radiology administrator looking to invest in a new technology (e.g., CT scanner), may use the program 110 to search the database 113, 114 to identify institutional providers fitting a similar profile (e.g., bed size, patient population served, geography) whose workflow and performance data are in the upper 10% of their reference peer group. The administrator may then review the technology profile of these institutions to determine the specific type of technology being used, and use this information to assist in their own technology selection.

Technology vendors have a unique opportunity to utilize the database 113, 114, to determine the impact a specific technology may have on workflow. For example, a technology provider (e.g., PACS vendor) is planning to release a new software upgrade, which has redesigned hanging protocols for CT and MRI. The vendor has access to the workflow data of its customers using the older software version and can directly compare workflow data after implementation of the new software in these same customers. Assuming all other variables remain constant (e.g., radiologists, technologists, acquisition technologies), the technology vendor would have the ability to directly measure "before and after" workflow data to determine the relative impact the specific technology has on workflow. Vendors could potentially use this data for comparative analysis (using anonymized data), and identify opportunities for innovation and improvement.

Thus, current medical imaging practices have attempted to counteract declining reimbursements by increasing revenue through increased productivity and operational efficiency. While these efforts have produced positive gains, they remain somewhat limited by the relative absence of objective data-driven workflow analysis. The creation of a comprehensive workflow database 113, 114 provides additional opportunity for workflow improvement through enhanced knowledge, which can in turn be used for technology innovation. A number of innovative strategies are included in the present invention, including customizable external pacers, computerized workflow analysis through embedded electronic auditing tools, and the creation of automated workflow templates tied to data-driven "best practice" guidelines.

The present invention provides for the simultaneous improvement of workflow and clinical outcomes, taking into account the unique attributes of each individual patient, provider, examination, and technology. In the end, the database 113, 114 and derived analytics provide a tool of empowerment; for enhanced education, training, research, technology development, and end-user performance.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following Claims.

What is claimed is:

1. A computer-implemented method of instituting a quality program in a medical application, comprising:
    recording a plurality of data elements into a database of a computer system, said data elements including a profile of a patient, a profile of a medical institution at which said patient was examined, imaging examinations performed on said patient, an examination profile of said patient, and a profile of an acquisition device used to perform said imaging examinations;
    performing a computerized measure of examination complexity based on said plurality of data elements and past performance measures and clinical outcomes of a service provider recorded in said database; and
    deriving an estimated examination interpretation time based upon said examination complexity, said estimated examination interpretation time which includes an individual user profile related to user experience, training, historical record of interpretation, speed, accuracy, and examination-specific attributes;
    wherein said estimated examination interpretation time is used to evaluate user efficiency.

2. The method of claim 1, further comprising:
    performing a computerized retrospective analysis of said past performance measures and said clinical outcomes by said service provider using data recorded in said database.

3. The method of claim 1, wherein said quality program is instituted to reflect and compare differences in service provider community, education, training, experience, supporting technology, institutional profile, and geography.

4. The method of claim 2, wherein said computerized retrospective analysis is continuously updated.

5. The method of claim 2, further comprising:
    providing an incentive to said service provider to review said computerized measure of examination complexity and said computerized retrospective analysis, to determine whether at least one of education or training is required.

6. The method of claim 2, further comprising:
    changing said user profile to reflect productivity changes.

7. The method of claim 3, further comprising:
    providing feedback, on a display of said computer system, to said service provider based upon said clinical outcomes, and efficiency measures.

8. The method of claim 7, further comprising:
    providing automated workflow templates with increased quality measures for said examination and for said user profile.

9. The method of claim 7, further comprising:
    incorporating electronic auditing tools into an analysis of user performance and comparing performances between users.

10. The method of claim 7, further comprising:
    identifying quality deficiencies in examination interpretation based upon said user profile; and
    providing representative individualized training to said user.

11. The method of claim 7, further comprising:
    performing comparative analysis of technology performance to determine technology impact on workflow.

12. The method of claim 6, further comprising:
    changing said estimated examination interpretation time based upon a correlation with actual interpretation times.

13. The method of claim 12, further comprising:
    providing a user with a personal estimated interpretation time along with a numerical measure for said examination complexity.

14. The method of claim 13, further comprising:
    providing a pacer alert to said user to inform said user when said estimated interpretation time has elapsed.

15. The method of claim 14, wherein said pacer alert is an auditory alert.

16. The method of claim 14, wherein said pacer is used to slow down a user's interpretation time to optimize diagnostic accuracy.

17. The method of claim 15, further comprising:
    providing said pacer alert to said user based upon when predetermined quality assurance deficiencies are detected.

18. The method of claim 16, wherein said user is a radiologist.

19. The method of claim 8, further comprising:
    recording to said database, all individual user human-computer interactions throughout interpretation of said imaging examination; and
    performing workflow analysis of said interactions, automated playback of said interactions, and correlation of said interactions with stored clinical, technical and performance data for productivity, workflow, and outcomes analysis.

20. The method of claim 8, further comprising:
    creating best practice automated workflow templates customized to the user, to a technology employed, and a clinical context.

21. The method of claim 19, further comprising:
recording, tracking and analyzing user visual interactions using an eye tracking system; and
incorporating data from said visual interactions into said automated workflow templates.

22. A computer system which institutes a quality program in a medical application, comprising:
at least one memory which contains at least one program which comprises the steps of:
recording a plurality of data elements into a database of a computer system, said data elements including a profile of a patient, a profile of a medical institution at which said patient was examined, imaging examinations performed on said patient, an examination profile of said patient, and a profile of an acquisition device used to perform said imaging examinations;
performing a computerized measure of examination complexity based on said plurality of data elements and past performance measures and clinical outcomes of a service provider recorded in said database; and
deriving an estimated examination interpretation time based upon said examination complexity, said estimated examination interpretation time which includes an individual user profile related to user experience, training, historical record of interpretation, speed, accuracy, and examination-specific attributes;
wherein said estimated examination interpretation time is used to evaluate user efficiency; and
at least one processor which executes the program.

23. A non-transitory computer readable medium containing executable code which institutes a quality program in a medical application, comprising:
recording a plurality of data elements into a database of a computer system, said data elements including a profile of a patient, a profile of a medical institution at which said patient was examined, imaging examinations performed on said patient, an examination profile of said patient, and a profile of an acquisition device used to perform said imaging examinations;
performing a computerized measure of examination complexity based on said plurality of data elements and past performance measures and clinical outcomes of a service provider recorded in said database; and
deriving an estimated examination interpretation time based upon said examination complexity, said estimated examination interpretation time which includes an individual user profile related to user experience, training, historical record of interpretation, speed, accuracy, and examination-specific attributes;
wherein said estimated examination interpretation time is used to evaluate user efficiency.

* * * * *